(12) United States Patent
Suga et al.

(10) Patent No.: US 6,661,915 B1
(45) Date of Patent: Dec. 9, 2003

(54) ILLUMINATION VARIABLE COLORIMETRIC METHOD AND COLORIMETER

(75) Inventors: Nagaichi Suga, Tokyo (JP); Takao Sumiyoshi, Tokyo (JP); Hideaki Kodachi, Tokyo (JP)

(73) Assignee: Suga Test Instruments, Tokyo (JP)

( * ) Notice: Subject to any disclaimer, the term of this patent is extended or adjusted under 35 U.S.C. 154(b) by 580 days.

(21) Appl. No.: 09/625,494

(22) Filed: Jul. 25, 2000

Related U.S. Application Data

(63) Continuation-in-part of application No. 09/023,563, filed on Feb. 13, 1998, now abandoned.

(51) Int. Cl.⁷ .......................... G06K 9/00; G01N 21/25; H04N 1/46
(52) U.S. Cl. .......................... 382/162; 356/405; 358/509
(58) Field of Search ................................ 382/162, 167, 382/168, 254, 260, 266, 274, 275, 286, 305; 356/402, 405, 406, 408, 413, 425, 421, 422; 359/19, 267; 358/504, 509, 519, 518, 520

(56) References Cited

U.S. PATENT DOCUMENTS

| | | | | |
|---|---|---|---|---|
| 3,875,453 A | * | 4/1975 | Thornton, Jr. | 313/487 |
| 4,150,898 A | * | 4/1979 | Suga | 356/405 |
| 4,256,131 A | * | 3/1981 | De Remigis | 137/3 |
| 4,278,538 A | * | 7/1981 | Lawrence et al. | 209/580 |
| 4,291,985 A | * | 9/1981 | Tsujimura | 356/408 |
| 4,685,071 A | * | 8/1987 | Lee | 382/162 |
| 5,153,751 A | * | 10/1992 | Ishikawa et al. | 359/13 |
| 5,272,518 A | * | 12/1993 | Vincent | 356/405 |
| 5,485,284 A | * | 1/1996 | Shono et al. | 358/504 |
| 5,570,192 A | | 10/1996 | Terauchi et al. | 356/407 |
| 5,717,783 A | | 2/1998 | Endo et al. | 382/167 |
| 5,771,311 A | | 6/1998 | Arai | 382/162 |
| 5,831,740 A | * | 11/1998 | Terauchi | 356/402 |
| 5,850,472 A | | 12/1998 | Alston et al. | 382/162 |
| 5,854,680 A | | 12/1998 | Rakitsch | 356/406 |
| 5,986,767 A | * | 11/1999 | Nakano et al. | 356/419 |

* cited by examiner

Primary Examiner—Bhavesh M. Mehta
Assistant Examiner—Kanji Patel
(74) Attorney, Agent, or Firm—Wenderoth, Lind & Ponack L.L.P.

(57) ABSTRACT

A method and apparatus allows mutual comparison of a mode of appearance of a color by the visual sense with a mode of appearance of the color from a calorimetric value from a calorimeters, and establishes a corresponding relationship between both evaluations. In the illumination variable calorimetric method and colorimeter, an illumination adjustment mechanism and an illumination measurement light receiver are disposed in a measurement optical path of an optical portion. After an illumination is adjusted to a predetermined illumination while a standard plate is placed on the surface of a sample table, standard adjustment is effected. Thereafter, measurement is started by placing a sample on the sample table, and the illumination of the sample table is varied by the light quantity adjustment mechanism so that changes in hue, saturation and lightness of a surface color of the sample and each color difference value with respect to the change of illumination of the same sample can be measured and displayed.

9 Claims, 9 Drawing Sheets

PRIOR ART

Standard adjustment is made at 6,310 lx by using accessorial white plate

ILLUMINATION VARIABLE COLORIMETRIC METHOD AND COLORIMETER

This application is a Continuation-In-Part of application Ser. No. 09/023,563, filed Feb. 13, 1998 now abandoned.

BACKGROUND OF THE INVENTION

An optical method using a colorimeter for an evaluation of discoloration and fading of colors in a weathering (light-fastness) test has been created. However, it has been mainly used for a grade judgement of fastness in various industrial fields, such as in the dyeing industry.

In the visual sense, judgement of a sample color that is approximate to black or to another dark sample color is apt to be difficult, and saturation, lightness and color difference are likely to be judged to be smaller values if an illumination with a normal light source $D_{65}$, etc., is low. Therefore, the selection of brightness is of importance in the evaluation of colors.

Evaluation of discoloration and fading with existing colorimeters is made by using a colorimetric value after adjustment to a standard value with an accessorial standard plate, irrespective of the brightness/darkness of the sample. The present invention relates to an illumination (luminance) variable calorimetric method and a colorimeter in which the illumination (luminance) of a sample surface is adjusted by taking the brightness/darkness of the sample or the state of hue, saturation and lightness of the sample into consideration when determining the colorimetric value.

The conventional colorimeters (e.g. FIG. 4) are those which measure various measurement values of colors of reflecting and transmitting objects under conditions of standard lights A, C and $D_{65}$, and so forth. However, these conventional calorimeters do not determine the three attributes (hue, saturation and lightness) of a color, a colorimetric value and a color difference value corresponding to a change of illumination when the illumination of a sample surface is changed to determine an optimum illumination range in consideration of the attributes of the sample surface. None of the conventional colorimeters have solved these problems to the best knowledge of the present inventor.

The judgement of colors and the evaluation of discoloration/fading, contamination, etc., have been made by the visual sense judgement of people, while optical methods using a colorimeter have also been carried out. The conventional calorimeters involve a problem in that they cannot determine the three attributes (hue, saturation and lightness) of a color, the calorimetric value, and the color difference value corresponding to the change of illumination when the illumination is changed so as to determine an optimum illumination range in consideration of the attributes of the sample surface. In the case of the visual sense judgement of discoloration, fading, etc., the grading of the fading and the judgement of the color difference pairs are difficult, particularly when the color of a sample is approximate to black or is a dark color, or when the illumination of the light source used for illumination is low.

SUMMARY OF THE INVENTION

The inventor of the present invention has developed a system which can change the illumination (luminance) of a normal light source inside a calorimetric standard illuminant, apparatus. As a result, the judgement results of a plurality of observers become close to being identical by increasing the illumination of the normal light source when the sample has a dark color.

The present inventor has developed the technical concept described above and has further developed a calorimeter having the function of varying the illumination so as to bring both the evaluation results of a color into conformity in the evaluation of color judgement, etc.

The illumination variable calorimetric method and the calorimeter described above are equipped with a light power adjustment mechanism and an illumination measurement light receiver, and eliminate the drawbacks of conventional colorimeters and the disadvantages resulting from a color discrepancy between the visual sense and the calorimeter.

The present invention relates to the measurement of colors which compares the mode of appearance of a color image by the visual sense and the mode of appearance of the color from a colorimetric value by a colorimeter with each other, makes it possible to establish a correspondence relationship between each of the evaluation results, and reflects the difference of the modes of appearance of the color for the observer on the calorimeter depending on high and low illumination.

The colorimeter comprises an optical portion shown in FIG. 1 and a measurement portion shown in FIG. 3. The optical portion comprises a measurement optical path 7 and a compensation optical path 6. In addition, an illumination adjustment mechanism 12 for varying the illumination, and an illumination measurement light receiver 10 are both provided in the measurement optical path 7.

After the illumination is adjusted to a predetermined value such as 6,310 1× while a standard plate having high weatherability is placed on the surface of a sample table 8 of the optical portion, adjustment of a standard value put on the standard plate is effected. A sample 14 is placed on the sample table 8 and a calorimetric value at 6,310 1× is measured. The illumination of the sample surface is varied to 3,160, 2,040, 1,000 and 540 1×, for example, by the illumination adjustment mechanism 12 and the illumination measurement light receiver 10.

The illumination variable calorimetric method and the colorimeter of the present invention measure changes in the three attributes (hue, saturation and lightness) of the surface color of the same sample, each calorimetric value and the color difference value for each color difference pair with respect to the change of illumination described above, and displays them.

DETAILED DESCRIPTION OF THE INVENTION

In the illumination variable calorimetric method and the colorimeter according to the present invention, the mode of appearance of the color imaged by the visual sense and the mode of appearance of the color from the calorimetric value by the colorimeter are compared with each, other. A corresponding relationship is established between the judgement and evaluation results of the visual sense and the calorimeter, and the difference in the mode of appearance of the color imaged by the observer, depending on a high and low illumination, is reflected on the calorimeter.

In the conventional visual sense judgement of discoloration, fading, etc., the grading of the fading and the judgement of the color difference pairs have been difficult, particularly when the color of the sample 14 is approximate to black or is a dark color, or when the illumination of the light source used for illumination is low. Judgement results of a plurality of the light source used for illumination is low. Judgement results of a plurality of observers become increasingly similar when the illumination of the normal light source is increased. In addition, in the case of the sample 14 described above, the mode of appearance of the color from the calorimetric value by the conventional colorimeter does not coincide with the mode of appearance of the color imaged by the visual sense, and disadvantages occur in many cases.

In order to further develop the concept described above and to bring the evaluation results of the visual sense and the colorimeter into conformity in the judgement of the colors, the present invention provides an illumination variable colorimetric method and a colorimeter which bring the mode of appearance of the color into conformity with that of the visual sense judgement by arbitrarily varying the illumination (luminance) of a sample surface in a plurality of stages.

Figure 1:
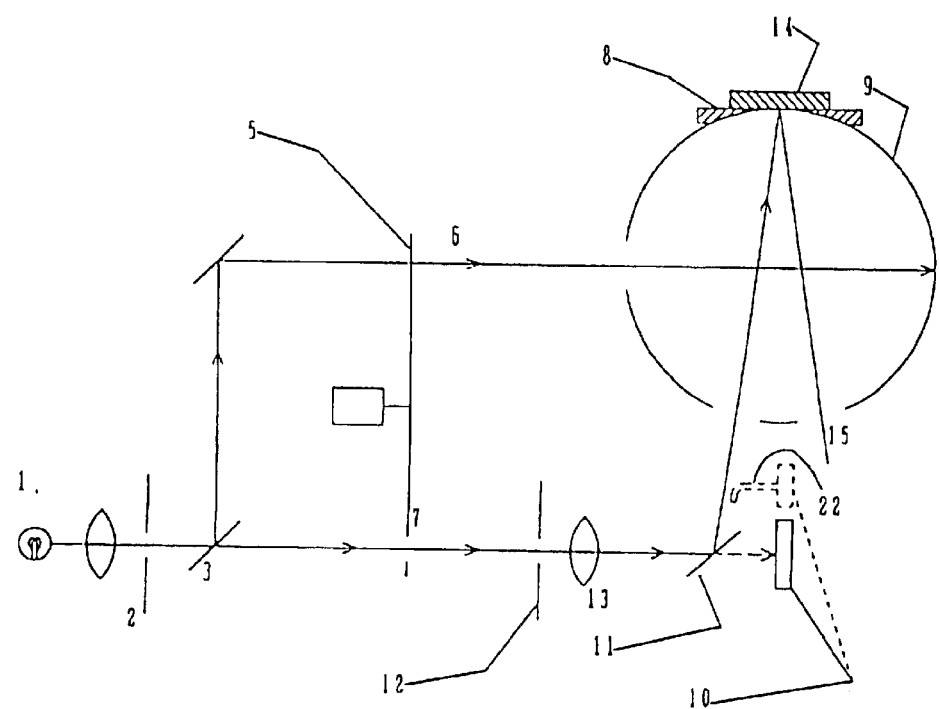
FIG. 1 is a schematic view showing an embodiment of an optical portion of the present invention.
Figure 3:
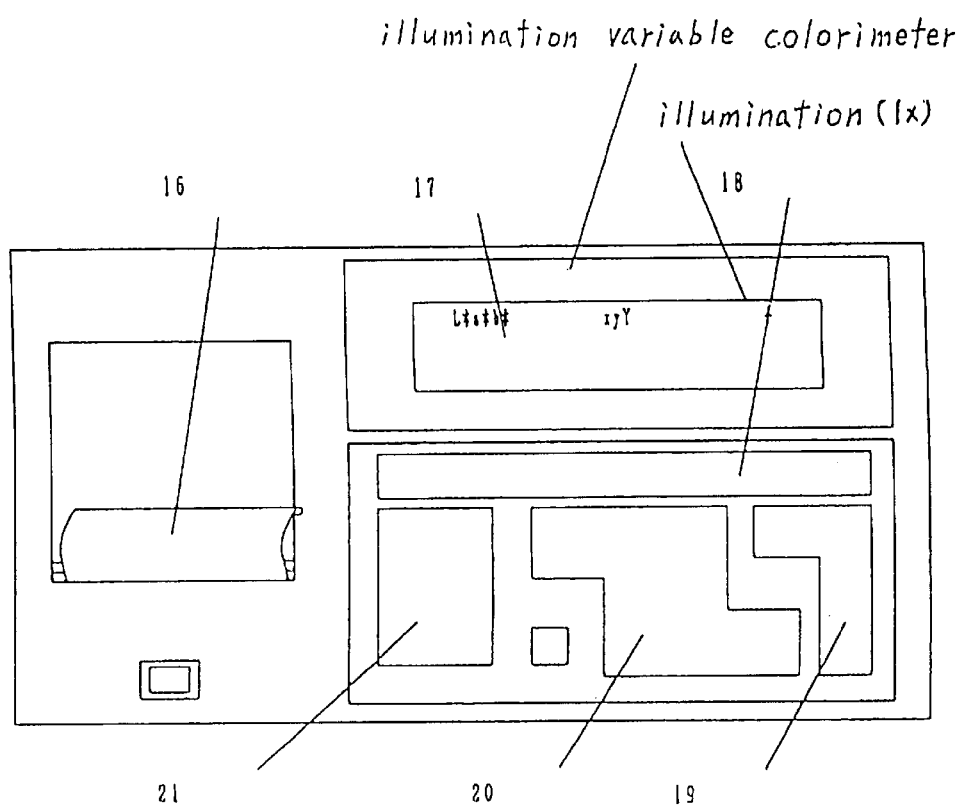
FIG. 3 is a front view showing an embodiment of a measurement panel of the present invention.
Figure 4:
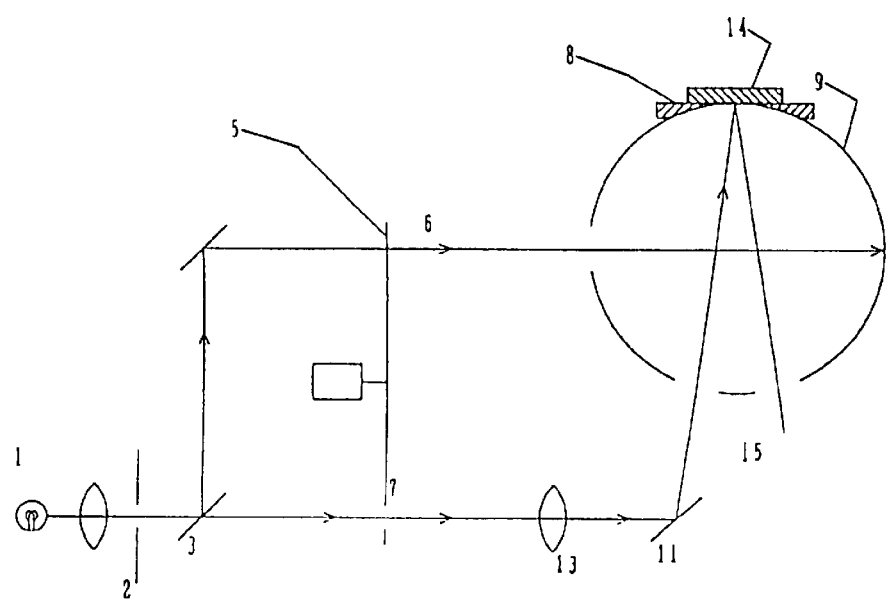
FIG. 4 is a schematic view showing an optical portion of the prior art.

The colorimeter according to the present invention comprises an optical portion shown in FIG. 1 and a measurement portion shown in FIG. 3. FIG. 1 shows an illumination adjustment mechanism 12 for changing the illumination of a sample surface, and shows an illumination measurement light receiver 10 for measuring the illumination of the surface of the sample 14 disposed in a measurement optical path 7. The illumination measurement light receiver 10 is operable to output electrical signals based on the level of illumination it detects. In addition, FIG. 1 shows a luminous flux switch 2, an optical path separating mirror 3, a reflecting mirror 4, an optical path switching rotary disc 5, a compensation optical path 6, a lens 13 and an optical trap 15. In this embodiment, an iris diaphragm, an optical attenuator formed by sandwiching a liquid crystal between polarizer plates, or a continuous subtractive filter can be used for the illumination adjustment mechanism 12, and the operation of the illumination adjustment mechanism 12 may either be manual or automatic.

FIG. 3 shows a printer 16, a display screen 17, a display lamp 18, a measurement key 19, a function key 20 and a numerical key 21.

A luminous flux from a light source 1 is transmitted through the illumination adjustment mechanism 12 via the measurement optical path 7 and is reflected by an optical path changing mirror 11 (i.e. reflecting mirrors 11a, 11b, 11c, shown in FIG. 2, or, similar mirrors) at a position in proximity to a lower part of an integrating sphere 9. The reflecting mirrors can be made to be movable by a moving device (not shown), so that the light from the light source 1 passes through the reflecting mirror. The mirror is positioned so that at least a portion of the light is redirected to be incident to a surface of the sample 14 inside the integrating sphere 9, and the other half is received by the illumination measurement light receiver 10. The integrating sphere 9 comprises three photoelectric light receivers (not shown). Each photoelectric light receiver comprises a Luther filter and a photoelectric sensor. The illumination measurement light receiver 10 is operable to measure the illumination of the surface of the sample 14 on a sample table 8. The illumination of the sample surface and the illumination measured by the illumination measurement light receiver 10 are mutually calibrated in advance, and the illumination of the sample surface is displayed on the display screen 17 of the measurement portion.

Figure 2A:
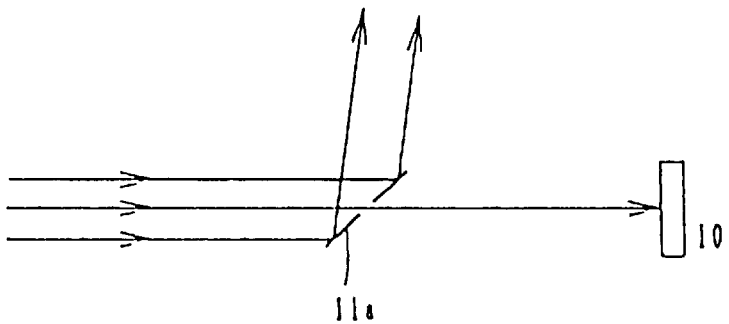
FIG. 2 is a schematic view showing an embodiment of an optical path changing mirror of the present invention.

In a first embodiment, a hole having a diameter of about 2 mm is formed at the center of the reflecting mirror 11a as shown in FIG. 2(a). A ray of light reflected by the reflecting mirror 11a is incident to the sample surface 14, while a ray of light passing through the hole is received by the illumination measurement light receiver 10.

Figure 2B:
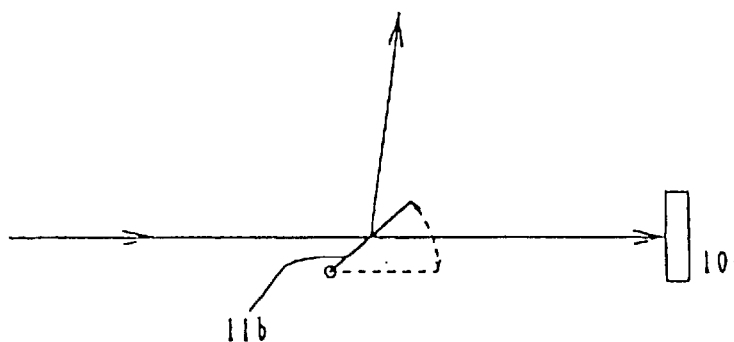

In a second embodiment shown in FIG. 2(b), the reflecting mirror 11b is angled with a point A as an axis (pivot), and the ray of light is received by the illumination measurement light receiver 10 only when the illumination display is indicated on the display screen 17 of the measurement portion.

Figure 2C:
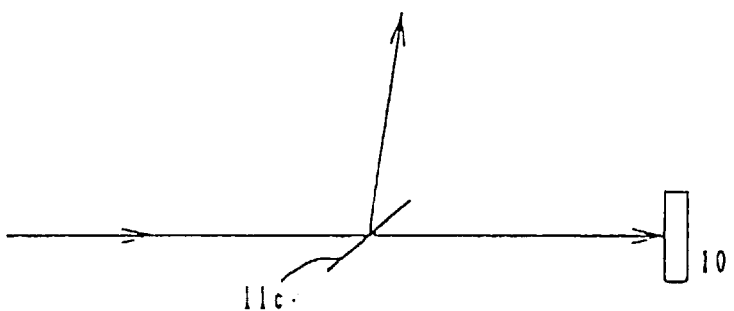
Figure 2D:
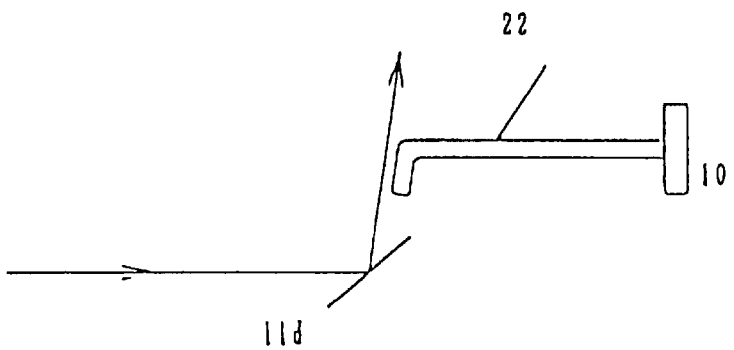

FIG. 2(c) shows a third embodiment for halving the luminous flux transmitted via the optical path 7 using a half mirror 11c. FIG. 2(d) shows a fourth embodiment including an illumination measurement light receiver 10 which receives light reflected by a reflecting mirror 11d, via a fiber waveguide 22. The fiber waveguide 22 is disposed at a position which does not impede the luminous flux incident to the sample surface.

The illumination, the colorimetric value, etc., are displayed on the display screen 17 and can also be printed out with the printer 16.

The optical portion represents the embodiment of the system of the integrating sphere 9 (FIG. 1), and the optical condition is an example of an 8/d system among those stipulated by the JIS standard. Incidentally, the optical condition is not particularly limited to the condition shown in FIG. 1, and a large number of changes and modifications can be made for the optical portion of the optical conditions stipulated by TIS Z 8722 (calorimetric method of object colors) without departing from the spirit of the present invention.

The mode of usage is as follows. While the accessorial standard plate is placed on the surface of the sample table 8, the illumination is adjusted and set. After the standard adjustment is effected, the measurement of the tristimulus values of X, Y, Z is started by placing the sample 14 on the sample table 8.

Generally, the measurement is carried out by arbitrarily dividing the illumination into a plurality of stages from high illumination to low illumination, and the results are plotted as a chromaticity diagram so as to grasp the mode of appearance of the color at each illumination. These results are then compared with the mode of appearance of the color from the visual sense judgement at the same illumination of the normal light source. In this case, the corresponding relationship of the judgement of both modes of appearance of the color, according to the present invention, can be identified.

The illumination variable colorimetric method and the calorimeter according to the present invention can also display the calorimetric values of standard lights A, C and $D_{65}$, and can grasp the mode of appearance of the color when the illumination is changed by various light sources. Further, the present invention can clarify the corresponding relationship of the modes of appearance of the color of both at metamerism by disposing the standard light described above in the standard illuminant apparatus.

Although the upper limit of the illumination range is set to about 6,000 1x (lux) in the embodiments of the present invention, there is no particular limitation, and a illumination can be further employed.

In the visual sense comparison method (JIS Z 8723) of the surface color, the normal light source preferably has the an illumination of at least 2,000 1x for colors approximate to black and for dark colors. In the color comparison of coatings (ISO 3668-1976), the illumination is stipulated as 1,000 1x or 4,000 1x.

Figure 5:
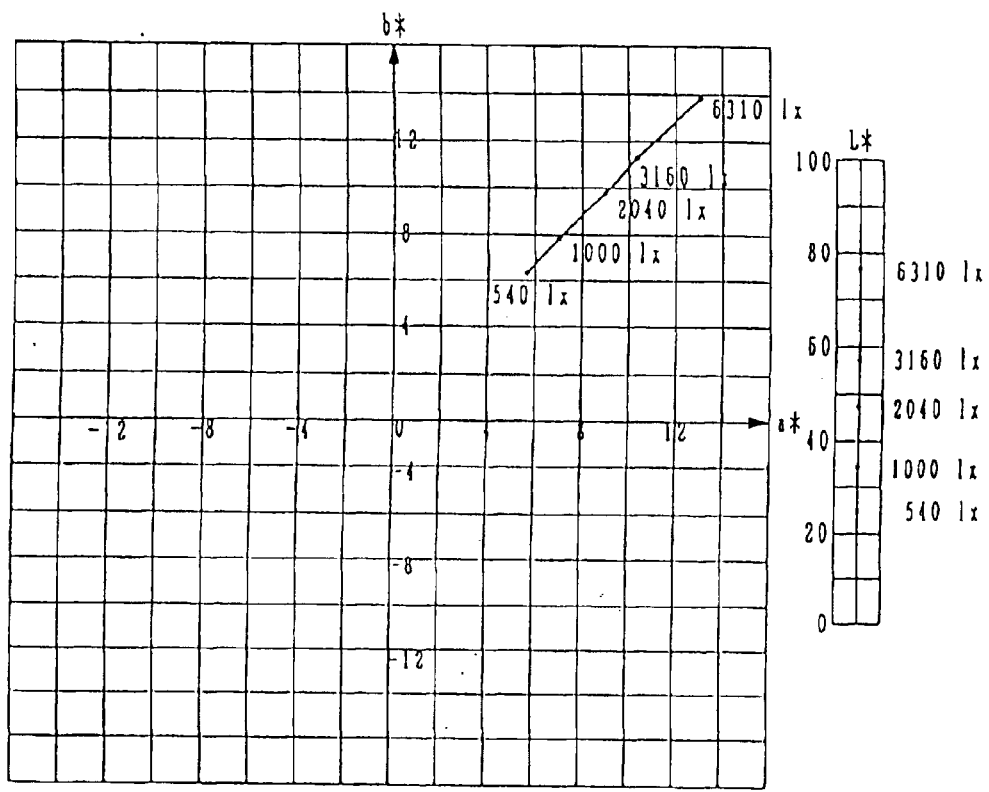
FIG. 5 is an H*a*b* chromaticity diagram of an orange sample measured by changing illumination in an illumination variable calorimetric method and a colorimeter according to the present invention.
Figure 6:
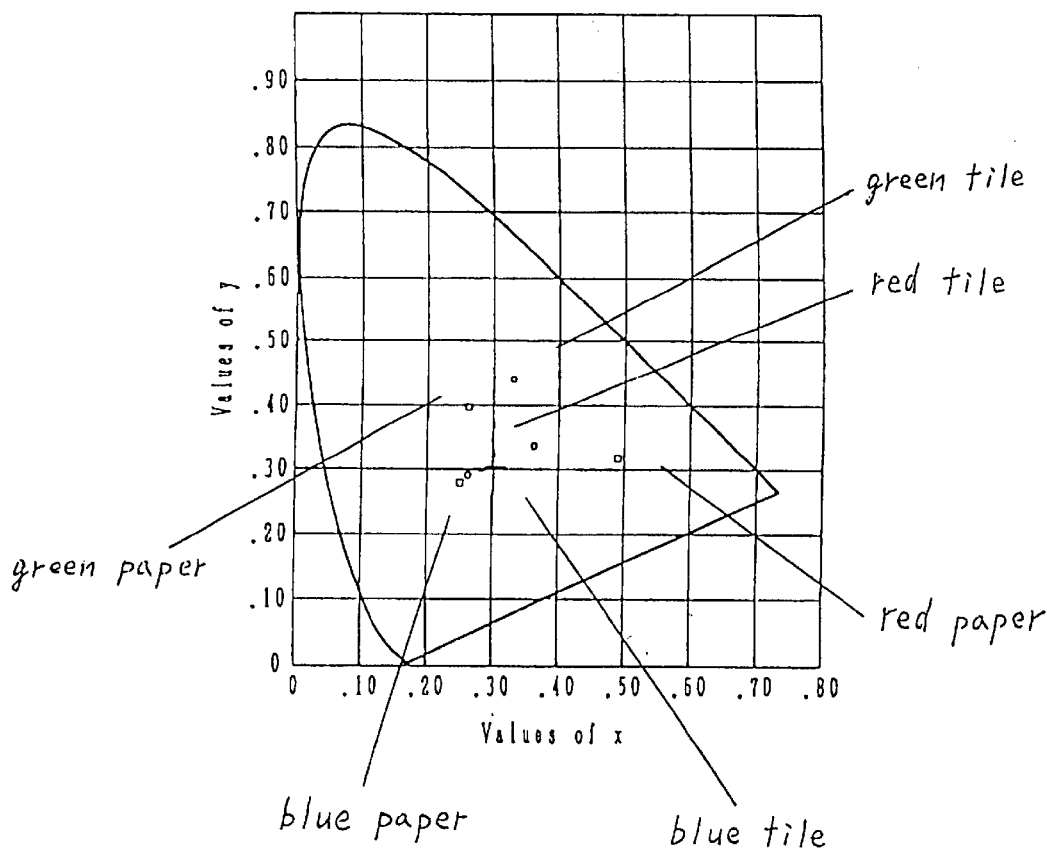
FIG. 6 is a C.I.E. x-y chromaticity diagram of red, green and blue samples measured by changing illumination by the illumination variable colorimetric method and the calorimeter according to the present invention.
Figure 7:
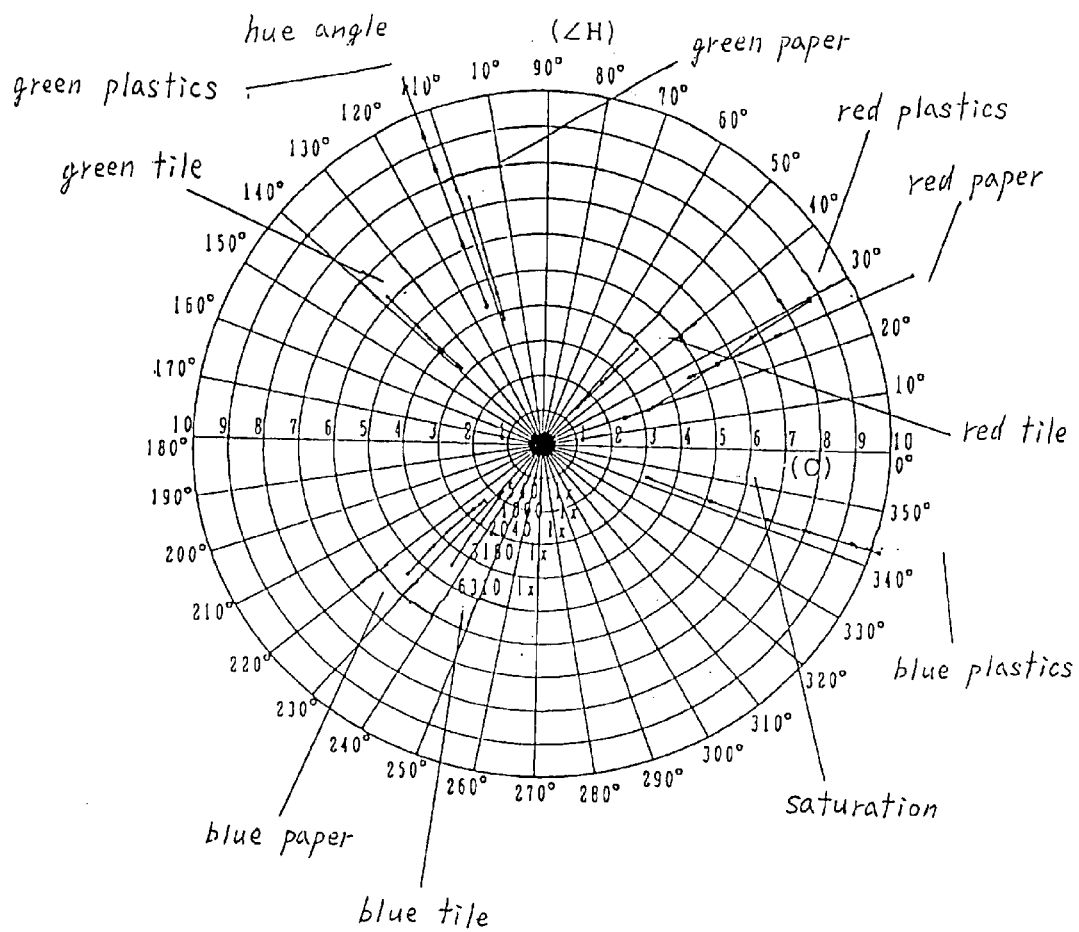
FIG. 7 is a C.I.E. L*c*h* chromaticity diagram of red, green and blue samples measured by changing illumination by the illumination variable calorimetric method and the calorimeter according to the present invention.
Figure 8:
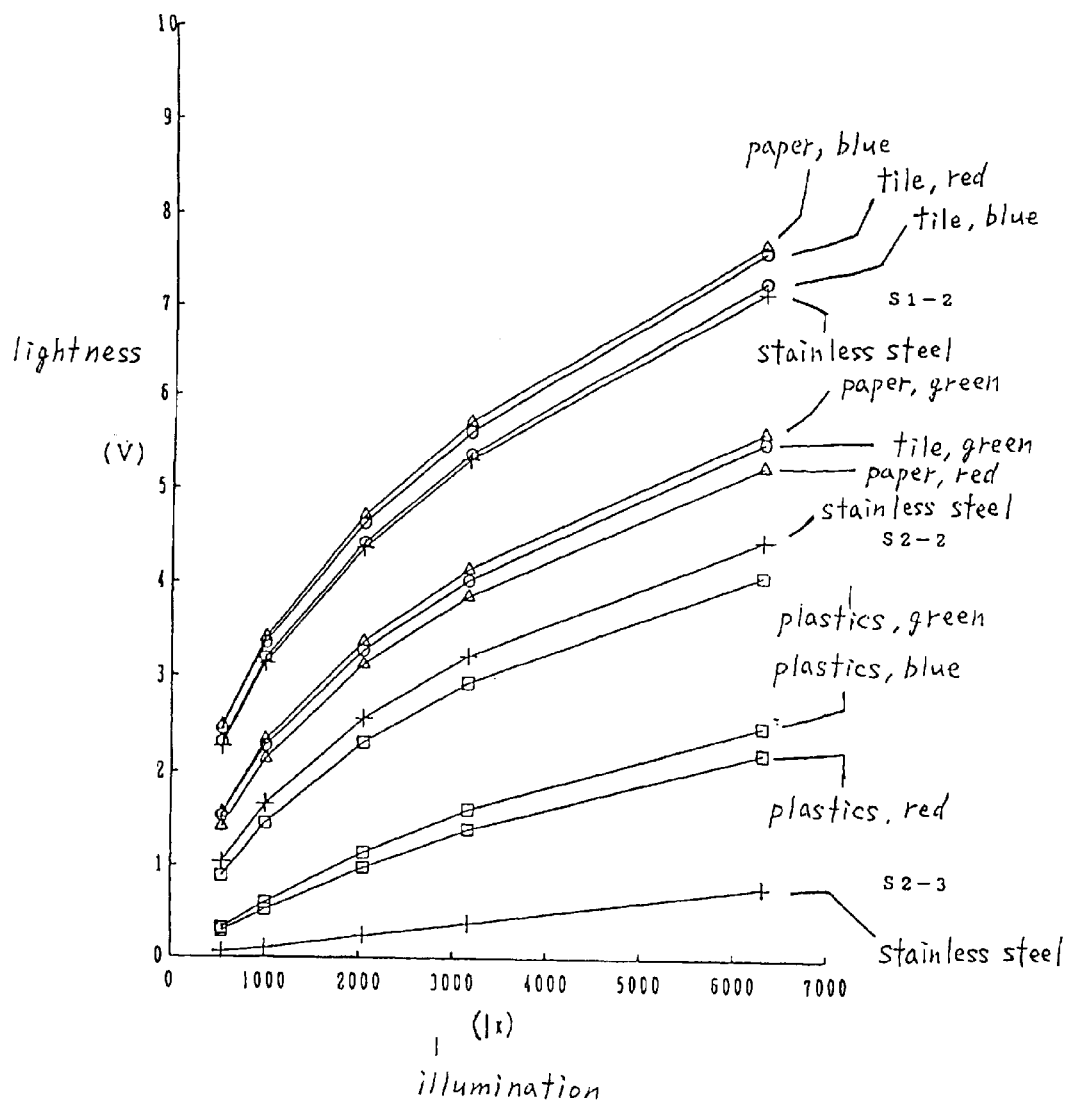
FIG. 8 is a relational diagram between illumination (1x) and lightness (V) of red, green, blue samples and a stainless sample measured by changing illumination by the illumination variable calorimetric method and the calorimeter according to the present invention.
Figure 9:
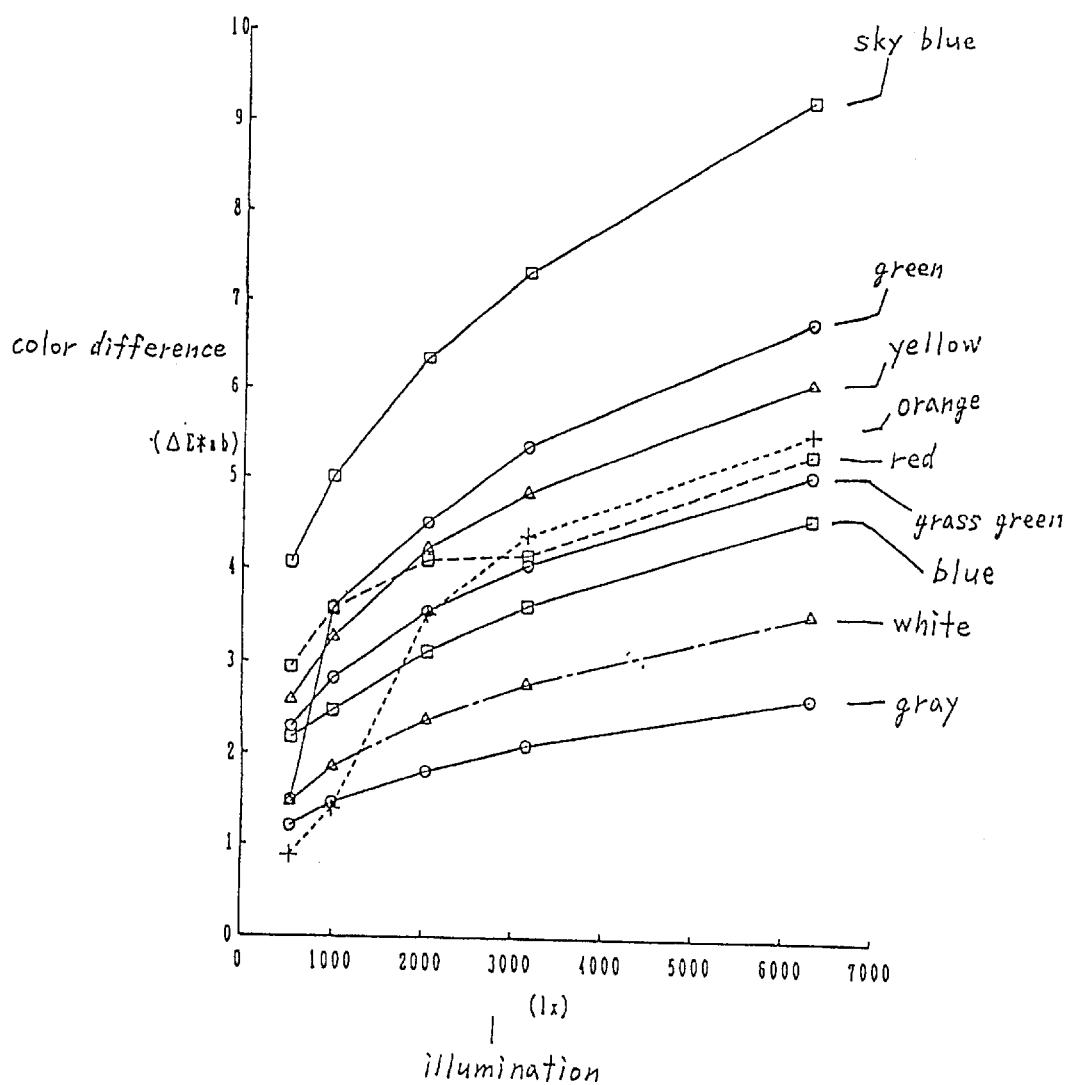
FIG. 9 is a relational diagram between illumination (1x) and lightness (V) of sky blue, green, yellow, orange, red, grass green, blue, white and gray samples when measured by changing illumination by the illumination variable calorimetric method and the colorimeter according to the present invention.

FIGS. 5, 6, 7, 8 and 9 show measurement diagrams using the illumination variable colorimetric method and the colorimeter according to the present invention. FIG. 5 is a chromaticity diagram of an L*a*b* display color system of an orange sample prepared by plotting the mode of appearance of the color after the standard adjustment is made by an accessorial standard plate at 6,319 1x and then changing the illumination. FIG. 6 is a C.I.E. x-y chromaticity diagram of red, green and blue samples prepared by plotting the mode of appearance of the colors when the illumination is changed under the conditions described above. FIG. 7 is a C.I.E. L*c*h* chromaticity diagram of the hue (<H) and the saturation (C) of the red, green and blue samples prepared by plotting the mode of appearance of the colors when the illumination is changed under the same conditions as described above. FIG. 8 is a relational diagram illustrating the relationship between the illumination (1x) and lightness (V) of each sample measured under the same conditions as described above. FIG. 9 is a relational diagram illustrating the relationship between the illumination (1x) and the color difference (ΔE*ab) of the color difference pair of each sample measured under the same conditions as described above.

The present inventor has recognized that colors approximate to black, and dark colors such as dark red and dark blue are one of the factors of the errors due to brightness when the illumination of the work surface is about 500 1x as in the prior art. Thus, the illumination variable colorimetric method and the colorineter of the present invention broadly change the illumination of the calorimeter so that the optimum illumination as viewed from the side of the sample surface (that is, the mode of appearance) matches the visual sense judgement.

The conventional colorimeters do not have a function for determining the three attributes of the color corresponding to a change of illumination when the illumination of the sample surface is changed, and can provide only one set of colorimetric values for one sample.

The present invention solves this problem by changing the illumination of the sample surface of the sample, and can numerically express the difference of the mode of appearance of the colors, and therefore has great benefits. Particularly, when the sample color is approximate to black or is a dark color, it has been difficult to grade fading and to judge color difference pairs, and the mode of appearance of the colors from the colorimetric values by the conventional colorimeters does not match the mode of appearance of colors by the visual sense, so that disadvantages occur in many cases.

The illumination variable colorimetric method and the calorimeter according to the present invention increase the illumination of the sample surface of the optical portion in the case of the sample described above, and match the mode of appearance of the colors from calorimetric values with the mode of appearance of the colors by the visual sense judgement. Therefore, the present invention provides great benefits in solving the matching problem.

FIGS. 5, 6, 7, 8 and 9 show the colorimetric values with various color display systems by using the illumination variable calorimetric method and the colorimeter for the chromaticity diagrams. These technical details can be used sufficiently for daily color management, and can provide great benefits. The present invention measures and displays those calorimetric values which cannot otherwise be stored and preserved, associates the mode of appearance of colors from the visual sense with the mode of appearance of the colors from the calorimetric values, and establishes the corresponding relationship between both evaluations.

Particularly, the color difference by the visual sense at the same illumination is contrasted with the contrast of the color difference (ΔE*ab) due to the change of illumination on the basis of the chromaticity diagrams described above, and this contrast is utilized for establishing the correspondence between both evaluations. Therefore, the present invention has great benefits.

What is claimed is:

1. A method for measuring color characteristics of a sample, the method comprising:

setting a colorimeter at standard tristimulus values of X, Y, Z based on a white standard plate under a specific level of illumination;

performing an initial measurement of tristimulus values of X, Y, Z of the sample under an initial illumination level, the initial illumination level comprising one of the specific level of illumination of the sample and another level of illumination of the sample;

varying the level of illumination of the sample relative to the initial illumination level;

performing at least one further measurement of tristimulus values of X, Y, Z of the sample during said varying of the level of illumination of the sample;

reporting the initial illumination level, and reporting the level of illumination used in said performing of at least one further measurement of tristimulus values of X, Y, Z of the sample; and plotting color measuring results on a chromaticity diagram based on the at least one further measurement of the tristimulus values of X, Y, Z of the sample.

2. A calorimeter for measuring color characteristics values of a sample, the colorimeter comprising:

a sample table for supporting the sample;

a light source operable to emit a measuring light;

an illumination adjustment mechanism;

an illumination measurement light receiver operable to measure the luminance of the measuring light emitted from said light source via said illumination adjustment mechanism;

an integrating sphere operable to receive the measuring light and to measure tristimulus values of X, Y, Z of the sample and further operable to integrate the measuring light, said illumination adjustment mechanism being operable to change a level of luminance of the measuring light while said integrating sphere measures the tristimulus values of X, Y, Z of the sample; and an optical path changing mirror operable to direct an optical path of the measuring light toward said integrating sphere and said illumination measurement light receiver.

3. A colorimeter as claimed in claim 2, further comprising at least one of a display unit operable to display the luminance of the measuring light and a chromaticity diagram based on the tristimulus values of X, Y, Z of the sample, and comprising a printer operable to print out the luminance of the measuring light and the chromaticity diagram.

4. A colorimeter as claimed in claim 2, wherein said optical path changing mirror comprises a reflecting mirror having a hole such that a portion of the measuring light passes through said hole and a remaining portion of the measuring light is reflected by said reflecting mirror to said integrating sphere.

5. A calorimeter as claimed in claim 2, wherein said optical path changing mirror comprises a half mirror shaped and arranged such that a portion of the measuring light passes through said half mirror and a remaining portion of the measuring light is reflected by said half mirror to said integrating sphere.

6. A calorimeter as claimed in claim 2, further comprising a fiber waveguide, shaped and arranged such that a portion of the measuring light from said optical path changing mirror passes through said fiber waveguide to said illumination measurement light receiver.

7. A calorimeter as claimed in claim 2, wherein said integrating sphere comprises at least one photoelectric light receiver having a Luther filter and a photoelectric sensor.

8. A calorimeter as claimed in claim 2, wherein said illumination measurement light receiver is further operable to output electrical signals based on the level of luminance detected.

9. A colorimeter as claimed in claim 2, wherein said optical path changing mirror comprises:

a reflecting mirror; and a device operable to move said reflecting mirror, wherein the measuring light from said light source passes through said reflecting mirror.

* * * * *